United States Patent
Garcia-Rubio

Patent Number: 5,808,738
Date of Patent: Sep. 15, 1998

[54] MULTIANGLE, MULTIWAVELENGTH PARTICLE CHARACTERIZATION SYSTEM AND METHOD

[75] Inventor: Luis Humberto Garcia-Rubio, Temple Terrace, Fla.

[73] Assignee: University of South Florida, Tampa, Fla.

[21] Appl. No.: 780,828

[22] Filed: Jan. 10, 1997

Related U.S. Application Data

[63] Continuation of Ser. No. 489,940, Jun. 13, 1995, abandoned, which is a continuation of Ser. No. 438,940, Jun. 13, 1995, abandoned.

[51] Int. Cl.⁶ .................................................. G01J 3/06
[52] U.S. Cl. .................... 356/309; 356/311; 356/300; 356/301; 356/303
[58] Field of Search .................................... 356/309, 311, 356/300, 301, 303

[56] References Cited

U.S. PATENT DOCUMENTS

| | | | |
|---|---|---|---|
| 2,436,104 | 2/1948 | Fisher | 356/303 |
| 4,900,113 | 2/1990 | Hatori | 356/303 X |
| 5,023,804 | 6/1991 | Hoult | 356/303 X |

*Primary Examiner*—Frank G. Font
*Assistant Examiner*—Reginald A. Ratliff
*Attorney, Agent, or Firm*—Allen, Dyer, Doppelt, Milbrath & Gilchrist, P.A.

[57] ABSTRACT

A system and method are provided for the characterization of a sample containing a macromolecule in solution. A light source illuminates the sample, generally in the ultraviolet-visible wavelength range, and a plurality of sensors that are radially disposed about the sample at a plurality of observation angles simultaneously sense the light energy emerging from the sample. An intensity spectrum is calculated as a function of wavelength for each observation angle, from which is calculated a particle characteristic such as shape, conformational change, composition, and particle size distribution. Both scattering and absorption data are utilized to provide complementary information.

22 Claims, 4 Drawing Sheets

MULTIANGLE, MULTIWAVELENGTH PARTICLE CHARACTERIZATION SYSTEM AND METHOD

This is a continuation of application Ser. No. 08/438,940 filed Jun. 13, 1995 abandoned.

CROSS-REFERENCE TO RELATED APPLICATION

This application is a continuation of application Ser. No. 08/489,940, filed Jun. 13, 1995 abandoned.

This invention was made with U.S. Government support under Grant N00014-94-1-0963 awarded by the Department of Navy. The Government has certain rights in this invention.

BACKGROUND OF THE INVENTION

1. Field of the Invention

The present invention relates to particle characterization and detection techniques and systems and, more particularly, to characterization and detection systems and methods using the light scattering and absorption properties of a particle.

2. Description of Related Art

The use of absorption spectroscopy and light scattering methods for the determination of the composition and the molecular weight of macromolecules and the weight of particles is well known in the art. Instrumentation for such methods is available for both static and flow measurements.

Until now absorption and light scattering have been considered to be separate and independent measurements, although the same physical phenomena are present in both techniques. In the ultraviolet-visible (uv-vis) portion of the electromagnetic spectrum, light scattering measurements are conducted at wavelengths where the chromophoric groups present in the macromolecule do not absorb. Light scattering data are typically utilized to measure particle size distributions and estimate the molecular weight of the particle. Light scattering data have been collected at multiple angles for a single wavelength.

Absorption spectroscopy is usually conducted in the spectral region in which scattering effects can be minimized. Absorption data are used to estimate particle concentration and chemical density and composition.

Theoretical Background

Under conditions of negligible absorption, and in the regime in which the Rayleigh-Debye-Gans approximations are valid, the angular dependence of the scattered intensity is given by:

$$\left.\frac{i_s}{I_0}\right)_\theta = \frac{2\pi^2[n(dn/dc)]^2 C(1+\cos\theta)}{N_A R^2 \lambda^4 (1/M + 2Bc)} \quad (1)$$

where all variables have their usual meaning. This equation (1) is the fundamental equation for the scattering of unpolarized light by nonabsorbing monodisperse polymer molecules in solution. In this equation the refractive index of the solution n and the specific refractive index increments dn/dc are inversely proportional to the wavelength $\lambda$, generally increasing the contrast and, therefore, the sensitivity of light scattering measurements as the wavelength is decreased. Furthermore, at a given angle $\theta$ the ratio $$(1+\cos^2\theta)/\lambda^4 \quad (2)$$

will also increase with increasing wavelength. For example, changing the wavelength from 600 to 300 nm will increase the ratio $i_s/I_o$ by a factor of 16.

If the effect of the shape of the particle is taken into consideration, Eq. (1) has to be corrected by the form factor $P(\theta)$:

$$\left.\frac{i_s}{I_0}\right)_\theta = \frac{2\pi^2[n(dn/dc)]^2 C(1+\cos^2\theta)P(\theta)}{N_A R^2 \lambda^4 (1/M + 2Bc)} \quad (3)$$

where $$P(\theta) = (1/N)^2 \sum_i \sum_j \sin(\mu r_{ij})/(\mu r_{ij}) \quad (4)$$

and $$\mu = (4\pi/\lambda)\sin(\theta/2) \quad (5)$$

Notice that consideration of the form factor in Eq. (1) introduces an additional dependence on the wavelength through Eqs. (4) and (5). For small angles, the form factor can be expressed in terms of the root-mean-square radius of gyration $R_g$:

$$\lim_{\theta \to 0} P(\theta) = 1 - \frac{16\pi^2 R_g^2 \sin^2(\theta/2)}{3\lambda^2} \quad (6)$$

Combining Eqs. (3)–(6) leads to an expression for the scattered intensity from dilute polydisperse polymer solutions:

$$\left.\frac{i_s}{I_0}\right)_\theta = \frac{2\pi^2[n_0(dn/dc)]^2 C(1+\cos^2\theta)\overline{M}_w C}{N_A R^2 \lambda^4 [1 + (16\pi^2/3\lambda^2)<R_g^2>_z \sin^2(\theta/2)]} \quad (7)$$

For particles of arbitrary shape in the Rayleigh-Debye-Gans regime, it has been shown that:

$$\left.\frac{i_s}{I_0}\right)_\theta = \left(\frac{9\pi^2 V_o}{2\lambda^4 R^2}\right) \left|\frac{m^2-1}{m^2+2}\right|^2 C(1+\cos^2\theta)P(\theta) \quad (8)$$

where $$m = \frac{n(\lambda) + ik(\lambda)}{n_0(\lambda)} \quad (9)$$

and $V_P$ represents the volume of the molecule.

SUMMARY OF THE INVENTION

As mentioned above, scattering measurements are typically conducted using a single wavelength of light energy. However, when one notes that the ratio given in Eq. (2) is a function of the wavelength and the angle $\theta$, the complementary nature of measurements where either the wavelength and/or the angle can be changed is reflected. If the uv-vis spectrum is recorded as a function of wavelength, it is clear from Eqs. (1) and (2) that the available redundant information will improve on the estimates, and the statistics, of the molecular weight M and the second virial coefficient B.

In addition, it can be noted from Eq. (7) that, even at small angles, by recording the spectrum as a function of the wavelength, improved resolution for $M_w$ and $(R_g^2)$ can be obtained. Furthermore, if it is recognized that the specific refractive index increments for complex macromolecules such as copolymers and proteins can be approximated as a weighted sum of the refractive index increments of the moieties in the polymer, and that the refractive indexes themselves are functions of the wavelength, then it is clear that the conditions required for the characterization of copolymers will be met by recording the uv-vis spectrum as a function of the angle of observation. In principle, depending on the relative magnitudes of the refractive indexes, it may be possible to extract information regarding the polymer composition. This, of course, is better accomplished if absorption is present.

In the case of absorbing macromolecules, Eqs. (8) and (9) indicate that, under the assumption of additivity of chromophore absorption, the combination of angular measurements at several wavelengths may allow for the estimation of the sample composition, molecular weight, and shape.

Since complementary information is available from both light scattering and absorption measurements, it is considered advantageous to conduct them simultaneously. The system and method of the present invention accomplish these simultaneous multiwavelength multiangle measurements that yield information on the size, shape, and composition of particles.

It is therefore an object of the present invention to provide a system and method for detecting and/or characterizing a particle such as a polymer or macromolecule in solution.

It is a further object to provide such a system and method for simultaneously providing a plurality of complete ultraviolet-visible intensity spectra at multiple angles of observation.

It is an additional object to calculate from measurements provided by such a system and method a reconstructed image of the particle under study.

It is another object to provide such a system and method for sensing and characterizing a particle in a flowing solution.

It is yet a further object to provide such a system and method for simultaneously measuring chemical composition and particle size.

It is yet another object to provide such a system and method for studying conformational changes and aggregation properties of a particle sample.

These and other objects are provided by the system and method of the present invention for the characterization of a sample containing a particle in suspension. Generally the particle should have a size generally in the range of 10 nm to 20 $\mu$m. The system comprises illumination means positioned to provide light energy to a volume portion of the sample. Typically the light energy is provided over a predetermined wavelength range encompassing the ultraviolet and visible portions of the spectrum, but it may also include the near-infrared portion.

A plurality of light-energy sensing means are radially disposed about the sample at a plurality of observation angles. This arrangment permits the simultaneous sensing of light energy emerging from the sample volume portion at the plurality of angles.

Further, the system comprises transducing means in communication with the sensing means. The transducing means provide from the sensed light energy a signal representative of an intensity spectrum as a function of wavelength for each observation angle. In a preferred embodiment the transducing means comprises a spectrophotometer card for communicating with a processor.

In order to provide particle size distribution, shape, conformational change, composition, and/or composition change information, software is loaded into the processor to perform the appropriate calculations.

The features that characterize the invention, both as to organization and method of operation, together with further objects and advantages thereof, will be better understood from the following description used in conjunction with the accompanying drawing. It is to be expressly understood that the drawing is for the purpose of illustration and description and is not intended as a definition of the limits of the invention. These and other objects attained, and advantages offered, by the present invention will become more fully apparent as the description that now follows is read in conjunction with the accompanying drawing.

DETAILED DESCRIPTION OF THE PREFERRED EMBODIMENTS

A description of the preferred embodiments of the present invention will now be presented with reference to FIGS. 1–4.

Figure 1:
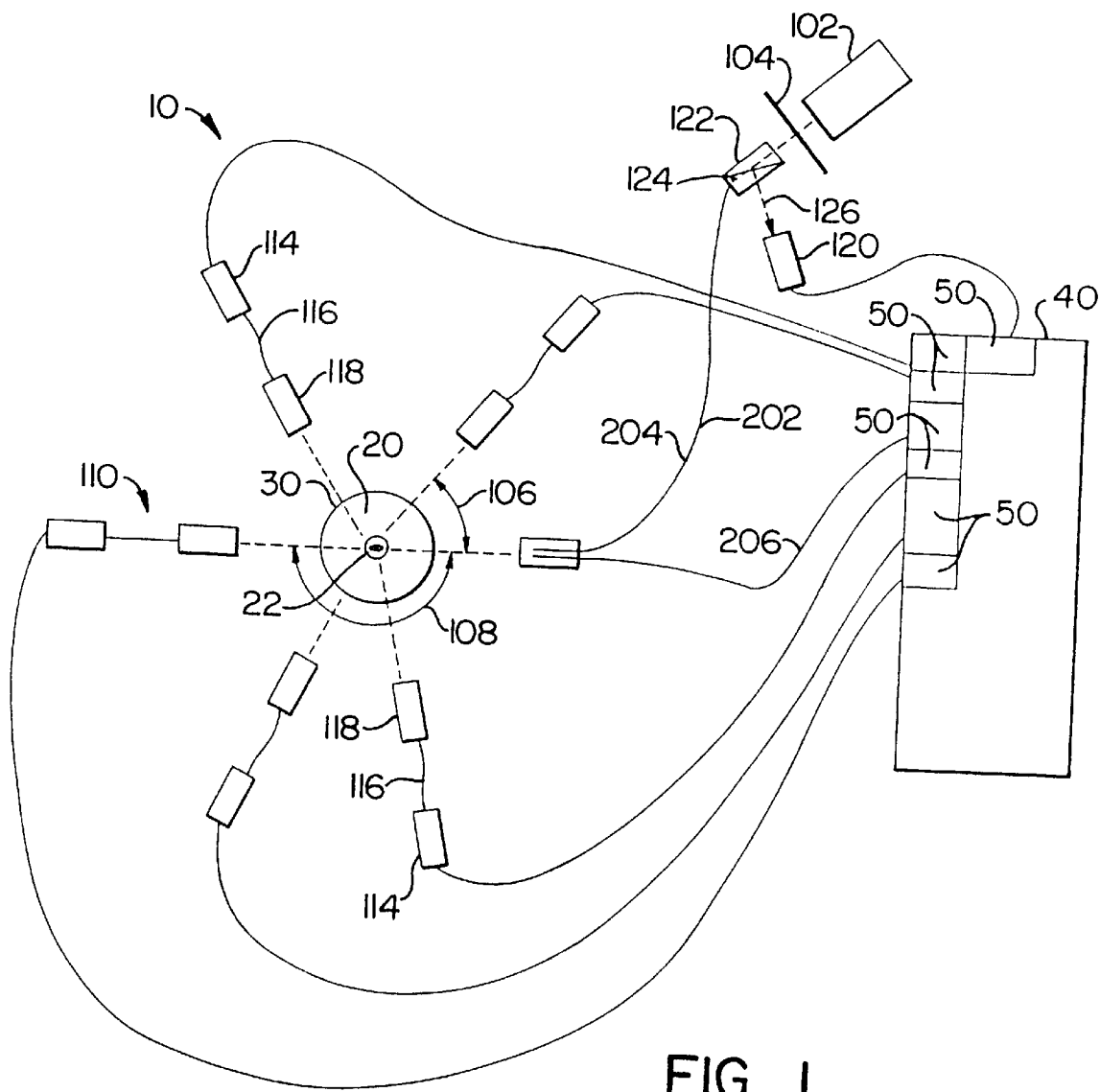
FIG. 1 is a schematic diagram of the multiangle multiwavelength system.
Figure 2A:
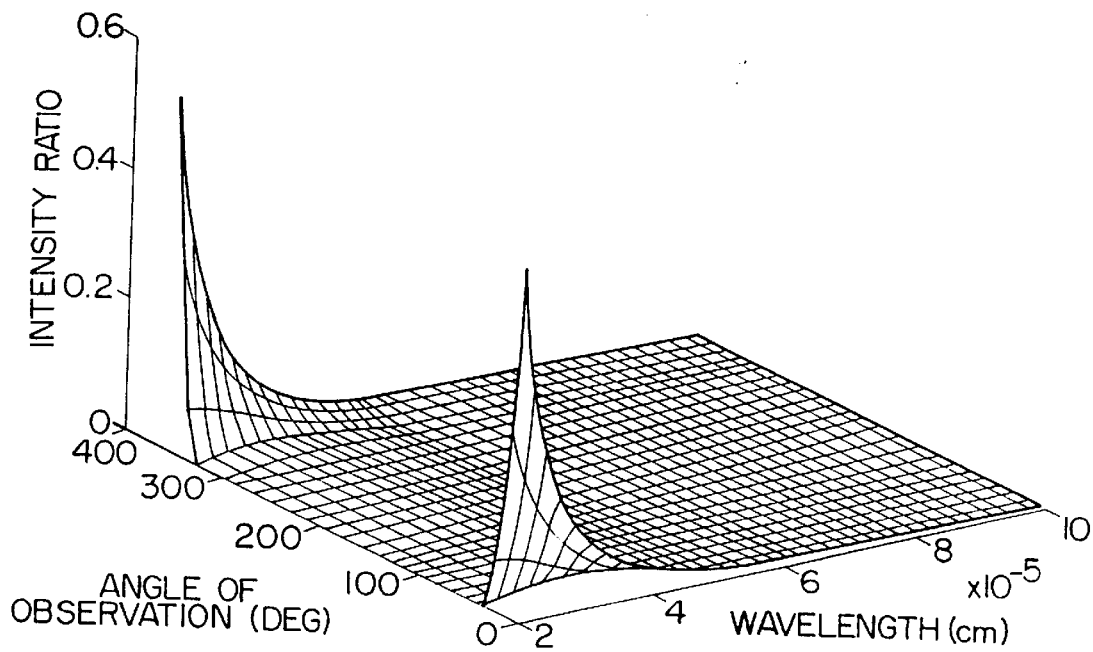
FIG. 2 illustrates theoretical intensity ratio spectra for (a) a sphere, (b) a thin rod, and a random coil illuminated with (c) unpolarized and (d) polarized light.
Figure 2B:
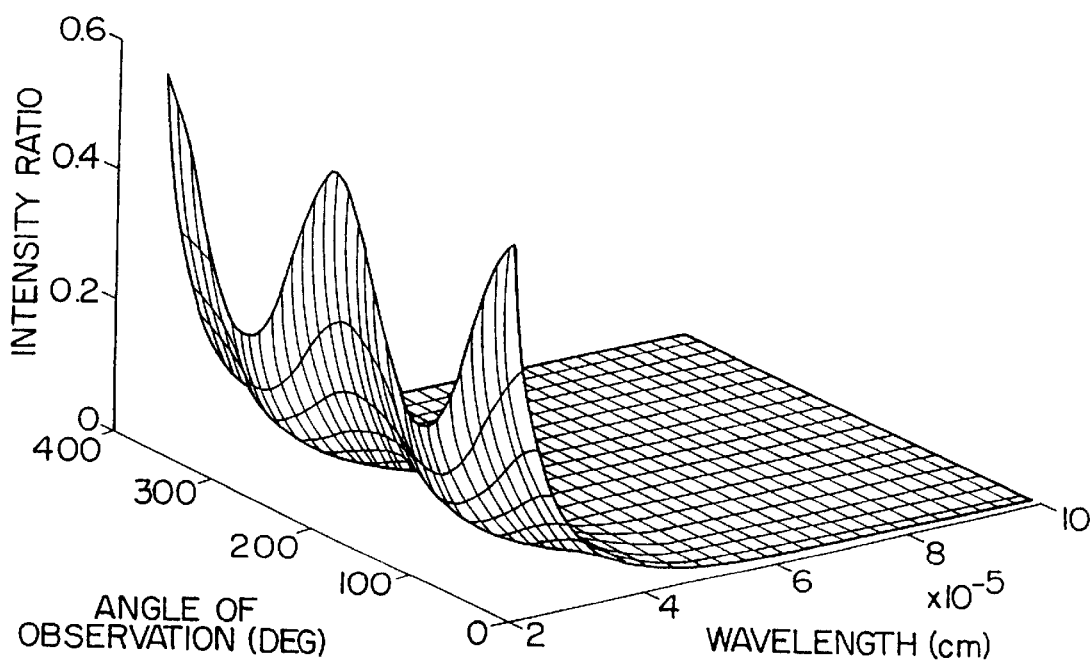
Figure 2C:
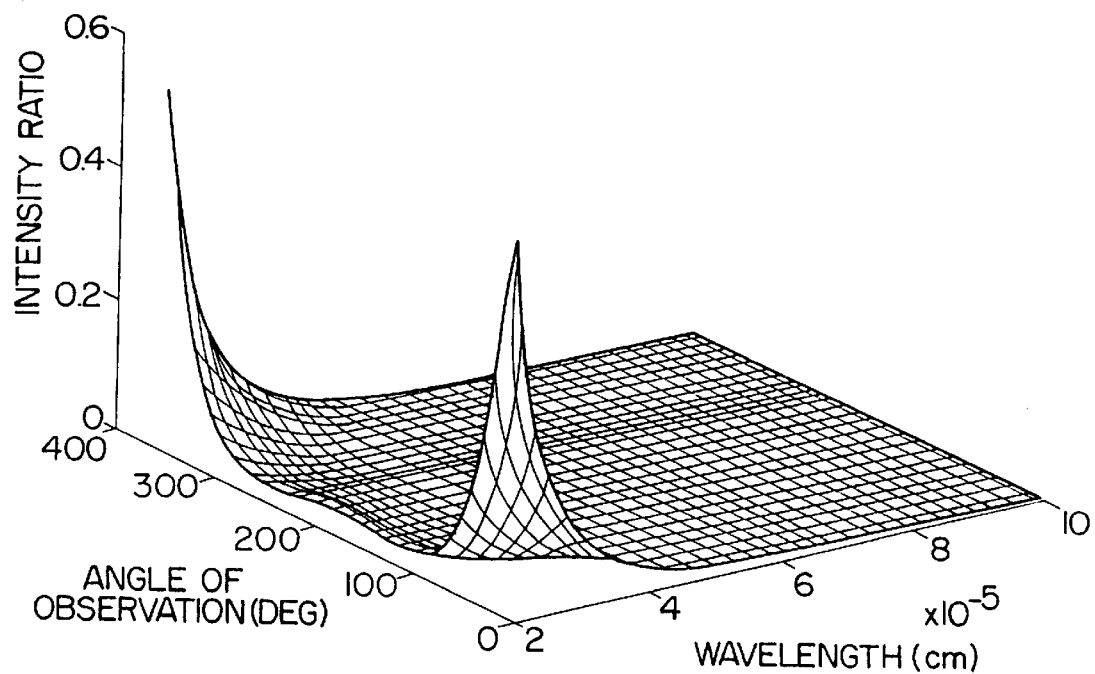
Figure 2D:
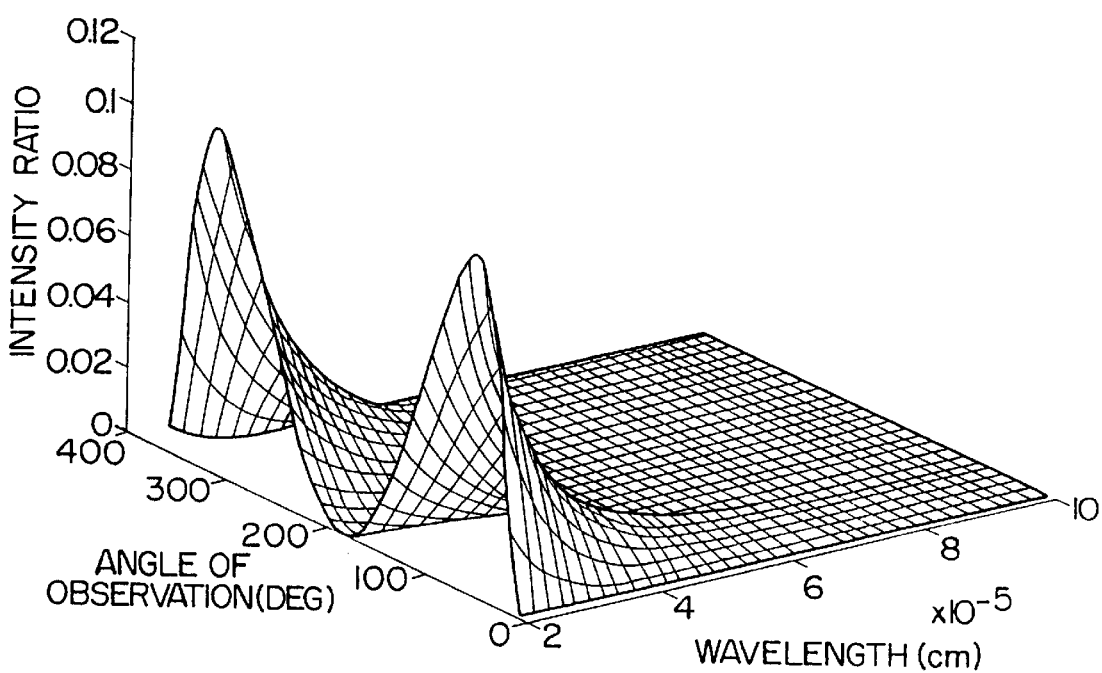

The system of the present invention, as shown schematically in FIG. 1, is for the characterization of a sample containing a particle in suspension such as a macromolecule or a polymer in solution. Typically the sample suspension 20 is contained in a sample cell 30 that is held in position on an optical bench.

The system 10 comprises illumination means positioned to provide light energy to a volume portion 22 the sample 20 over a predetermined wavelength range. Generally the wavelength range comprises the ultraviolet-visible (uv-vis) range, which can be provided by any of a number of sources, including a xenon light source 102. In a preferred embodiment the light is delivered to the sample 20 with an optical fiber 202.

In an alternate embodiment, the sample is illuminated with polarized light, produced by the insertion of a polarizer 104 in the incident light path between the light source 102 and the sample 20. In this embodiment the polarization properties of the sample are measured.

A plurality of light-energy sensing means is radially disposed about the sample 20 at a plurality of observation angles 106. These sensors are for simultaneously sensing light energy emerging from the sample volume portion 22 at the plurality of angles 106. It can be seen that alignment is important; so the sensors must be arrayed to permit the detection of an optimal quantity of light energy from the portion of the sample volume being illuminated. Typically the sensors are sensitive to light energy generally in the range of 180–1000 nm. In a preferred embodiment at least four sensors are used, with six being an optimal number. In order that the system be usable for transmission measurements, a first sensor 110 is placed at a 180 degree observation angle 108. Backscattering measurements are made by having the optical fiber 202 comprise a split optical fiber having an illumination portion 204 and a sensing portion 206, thus proving sensing capabilities at 0 degrees.

In a preferred embodiment each sensor comprises a charge-coupled device 114, to which light energy is fed by an optical fiber 116 that has received the light energy to be transmitted from a collimating lens 118, which produces a parallel beam of light energy from that impinging on it.

In order to compensate for fluctuations in the light energy provided by the light source, it is preferable, although not necessary, to also provide a reference sensor 120 for sensing light energy emerging directly from the light source 102. This may be accomplished, for instance, with the use of a beam splitter 122 between the light source 102 and the sample 20, the first pathway 124 leading to the sample and the second pathway 126 leading to the reference sensor 120.

An additional element of the system is transducing means in communication with the sensors. The transducing means provides from the sensed light energy a signal representative of an intensity spectrum as a function of wavelength for each observation angle 106. In a preferred embodiment the signal from each sensor is fed to a processor 40 into which a spectrophotometer card 50 has been integrated. In this system one spectrophotometer card 50 can handle one sensor input; therefore, there are provided the same number of spectrophotometer cards 50 as the number of sensors. In an embodiment having six sensors, for instance, six spectrophotometer cards 50 would be required.

Returning to the issue of normalization, the output from the reference sensor 120 is also fed to the a spectrophotometer card 50 in processor 40, wherein software means are provided for correcting the spectra for incident light energy intensity fluctuations.

Once the system 10 has captured the multiangle multiwavelength spectra for the sample being illuminated, software means resident in the processor 40 can be utilized to calculate any of a number of particle characteristics based on theories such as those outlined above. For example, particle size distribution, shape, particle composition, and changes with time in particle shape and composition can be calculated using imaging software from collected scattering and/or absorption spectra.

In FIG. 2 are shown calculated multiangle multiwavelength scattering spectra for a variety of ideal objects. In FIG. 2(*a*) is shown the intensity ratio of a spherically shaped particle as a function of the angle of observation and the angle of unpolarized incident light; in FIG. 2(*b*), that for a rod-shaped particle; in FIGS. 2(*c*) and (*d*), that for a coil-shaped particle, for, respectively, unpolarized and polarized light. These spectra are indicative of the type of information that can be obtained from the system and method of the present invention, including polarization properties of the sample.

Figure 3:
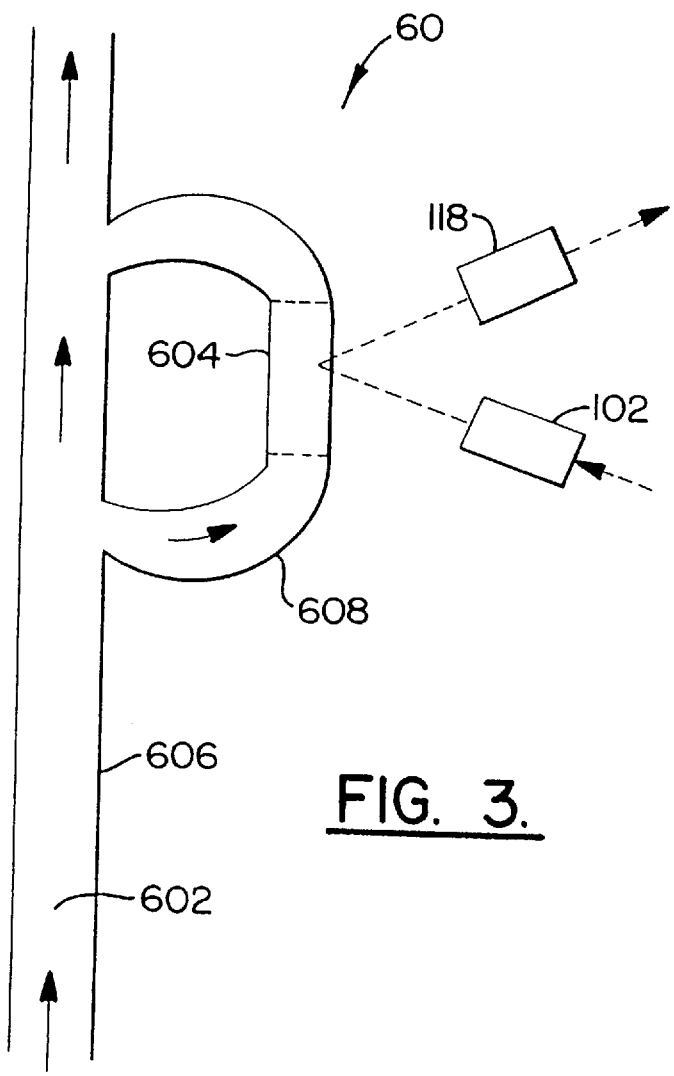
FIG. 3 shows the system in use for a flowing sample.

In an alternate embodiment 60 of the system of the present invention, multiangle multiwavelength spectra may be collected on a flowing sample (see FIG. 3). An exemplary use of this embodiment is for the detection of microorganisms in a water supply 602. In this case a particular particle characteristic is chosen to indicate the presence of the microorganism. The "sample cell" in this case comprises a diverted section 608 of pipe 606 having a transparent portion 604 through which measurements may be made.

Figure 4:
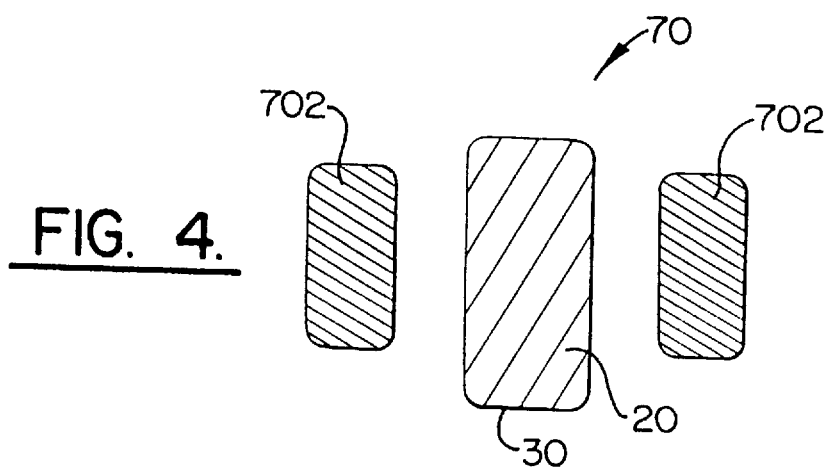
FIG. 4 shows the sample subjected to an electromagnetic field.

Yet another embodiment 70 of the system is illustrated in FIG. 4, which further comprises means for imposing an electromagnetic field on the sample, such as a magnet 702. Imposing such a field permits the measurement of the field-dependent properties of the sample.

It may be appreciated by one skilled in the art that many embodiments may be contemplated, including systems and methods for studying any particle in suspension in order to determine its presence, shape, functionality, and internal structure. Some exemplary embodiments, which are not meant to be limiting, include the characterization of components in blood samples, latex suspensions, metallic particles in solution, and microorganisms.

In the foregoing description, certain terms have been used for brevity, clarity, and understanding, but no unnecessary limitations are to be implied therefrom beyond the requirements of the prior art, because such words are used for description purposes herein and are intended to be broadly construed. Moreover, the embodiments of the apparatus illustrated and described herein are by way of example, and the scope of the invention is not limited to the exact details of construction.

Having now described the invention, the construction, the operation and use of preferred embodiment thereof, and the advantageous new and useful results obtained thereby, the new and useful constructions, and reasonable mechanical equivalents thereof obvious to those skilled in the art, are set forth in the appended claims.

What is claimed is:

1. A system for the characterization of a sample containing a particle in suspension, the particle comprising one of a macromolecule, a polymer, and a microorganism, and having a size generally in the range of 10 nm to 20 $\mu$m, the system comprising:

illumination means positioned to provide light energy to a volume portion of the sample, the light energy provided over a predetermined broadband wavelength range;

a plurality of light-energy sensing means radially disposed about the sample at a plurality of observation angles for simultaneously sensing a light energy spectrum corresponding to the broadband wavelength range emerging from the sample volume portion at the plurality of angles;

transducing means responsive to the predetermined broadband wavelength range in communication with the sensing means for providing from the sensed light energy a signal representative of an intensity spectrum as a function of wavelength for each observation angle; and processing means comprising means for simultaneously determining from the signal a scattering spectrum and an absorption spectrum for each observation angle and means for calculating from the scattering spectra and the absorption spectra a particle characteristic.

2. The system recited in claim 1, wherein the illumination means provides light energy generally over the ultraviolet-visible range.

3. The system recited in claim 2, wherein the illumination means comprises a xenon light source.

4. The system recited in claim 2, wherein each of the sensing means is sensitive to light energy generally in the range of 180–1000 nm.

5. The system recited in claim 2, further comprising means for normalizing each intensity spectrum for intensity fluctuations in the light energy provided by the illumination means.

6. The system recited in claim 2, wherein each sensing means comprises a charge-coupled device.

7. The system recited in claim 6, further comprising a plurality of collimating lenses, each collimating lens in optical contact with one of the charge-coupled devices and positioned between the sample and the respective charge-coupled device, each collimating lens for producing a parallel beam of light energy from the light energy impinging thereonto.

8. The system recited in claim 7, further comprising a plurality of optical fibers, each optical fiber forming the optical contact between each collimating lens and the respective one of the charge-coupled devices.

9. The system recited in claim 2, wherein the transducing means comprises a spectrophotometer card in electronic communication with the processor means and with the sensing means.

10. The system recited in claim 2, wherein the plurality of sensing means comprises a number comprising at least four sensors.

11. The system recited in claim 10, wherein the transducing means comprises a number of transducing means equal to the number of sensors.

12. The system recited in claim 9, wherein the calculating means comprises means for calculating a particle size distribution for the particle from at least one of the intensity spectra provided by a spectrophotometer card.

13. The system recited in claim 9, wherein the calculating means comprises means for calculating a shape of the particle from the plurality of intensity spectra.

14. The system recited in claim 13, wherein the calculating means further comprises means for calculating a conformational change in a shape of the particle with time from the plurality of intensity spectra provided by the plurality of spectrophotometer cards.

15. The system recited in claim 9, wherein the calculating means further comprises means for calculating a composition for the particle from the plurality of intensity spectra provided by the plurality of spectrophotometer cards.

16. The system recited in claim 15, wherein the calculating means further comprises means for calculating a change in composition of the particle with time for the particle from the plurality of intensity spectra provided by the plurality of spectrophotometer cards.

17. The system recited in claim 9, wherein the calculating means comprises means for calculating from the scattering spectra and the absorption spectra a conformation of the particle in suspension.

18. The system recited in claim 9, wherein the spectrophotometer card comprises a plurality of spectrophotometer cards, and wherein the calculating means comprises means for calculating for a flowing sample a change in a characteristic for the particle from the intensity spectra provided by the plurality of spectrophotometer cards, thereby permitting an on-line detection of a change in the particle characteristic.

19. The system recited in claim 1, wherein the illumination means comprises a polarized light source for measuring polarization properties of the sample.

20. The system recited in claim 1, further comprising means for imposing an electromagnetic field on the sample for measuring field-dependent properties of the sample.

21. A system for the characterization of a sample containing a particle in suspension, the system comprising:

a light source for providing light energy in a broadband wavelength range generally in the ultraviolet to the visible range to a volume portion of the sample;

six sensors radially disposed about the sample at six observation angles, a first sensor disposed generally 180 degrees from the light source, each sensor for sensing light energy emerging from the sample volume portion at the respective observation angle, each sensor providing an electronic signal representative of the sensed light energy;

a processor comprising means for simultaneously determining from the electronic signal a scattering spectrum and an absorption spectrum for each observation angle;

six spectrophotometer cards in electronic communication with the processor, each spectrophotometer card in electronic communication with one of the sensors, each spectrophotometer card providing from the electronic signal from each sensor a signal representative of an intensity spectrum as a function of wavelength; and imaging means resident in the processor for calculating from the scattering spectra and the absorption spectra a characteristic of the particle in suspension.

22. A method for characterizing a sample containing a particle in suspension, the method comprising the steps of:

illuminating a volume portion of the sample with light energy having a predetermined broadband wavelength range;

sensing light energy corresponding to the broadband wavelength range emerging from the sample volume portion at the plurality of observation angles;

transducing the sensed light energy into a signal representative of an intensity spectrum as a function of wavelength for each observation angle;

simultaneously determining from the signal a scattering spectrum and an absorption spectrum for each observation angle; and calculating from the scattering spectrum and the absorption spectrum a particle characteristic.

* * * * *

UNITED STATES PATENT AND TRADEMARK OFFICE
CERTIFICATE OF CORRECTION

PATENT NO. : 5,808,738
DATED : September 9, 1998
INVENTOR(S) : Luis H, Garcia-Rubio It is certified that error appears in the above-identified patent and that said Letters Patent is hereby corrected as shown below:

Column 1, Line 5:    Please strike lines 5 and 6

Column 1, Line 12    Insert the Following Heading --GOVERNMENT SUPPORT--.

Signed and Sealed this

Twenty-fifth Day of May, 1999

Attest:

Q. TODD DICKINSON

Attesting Officer      Acting Commissioner of Patents and Trademarks